United States Patent [19]

LaPierre et al.

[11] Patent Number: 4,899,008

[45] Date of Patent: Feb. 6, 1990

[54] DIRECT CATALYTIC ALKYLATION OF MONONUCLEAR AROMATICS WITH LOWER ALKANES

[75] Inventors: Rene B. LaPierre, Medford; Roger A. Morrison, Deptford, both of N.J.

[73] Assignee: Mobil Oil Corporation, New York, N.Y.

[21] Appl. No.: 324,483

[22] Filed: Mar. 16, 1989

Related U.S. Application Data

[63] Continuation-in-part of Ser. No. 205,563, Jun. 7, 1988, abandoned, which is a continuation of Ser. No. 64,630, Jun. 22, 1987, abandoned, which is a continuation-in-part of Ser. No. 879,786, Jun. 27, 1986, abandoned.

[51] Int. Cl.$^4$ .................................................. C07C 2/68
[52] U.S. Cl. ...................................................... 585/467
[58] Field of Search ......................................... 585/467

[56] References Cited

U.S. PATENT DOCUMENTS 4,085,156 4/1978 Frilette et al. ...................... 208/120
4,117,026 9/1978 Haag et al. .......................... 585/467

Primary Examiner—Curtis R. Davis
Attorney, Agent, or Firm—Alexander J. McKillip; Charles J. Speciale; Malcolm D. Keen

[57] ABSTRACT

Mononuclear aromatic hydrocarbons such as benzene and toluene are alkylated with $C_2$–$C_4$ paraffins in the presence of an acidic zeolite catalyst such as ZSM-5 in a one-step process to produce alkylaromatic products in high selectivity. Benzene and propane reactants produce predominantly $C_7$ to $C_9$ aromatics.

20 Claims, No Drawings

DIRECT CATALYTIC ALKYLATION OF MONONUCLEAR AROMATICS WITH LOWER ALKANES

CROSS REFERENCE TO RELATED APPLICATIONS

This application is a continuation-in-part of our prior application Ser. No. 205,563, filed 7 Jun. 1988 now abandoned which, in turn, was a continuation of application Ser. No. 064,630 filed 22 Jun. 1987 now abandoned which was a continuation-in-part of application Ser. No. 879,786, filed 27 Jun. 1986 now abandoned.

FIELD OF THE INVENTION

This invention relates to a process for converting an aromatic compound, such as benzene, to alkyl aromatic products by direct alkylation with a light alkane such as propane.

BACKGROUND OF THE INVENTION

In the past, the alkylation of aromatic hydrocarbons with non-heteroatom-containing hydrocarbons was achieved by one of two methods. The first method comprises the reaction of an aromatic hydrocarbon with an olefin such as ethylene or propylene. Alkylation of aromatic hydrocarbons with an olefin in the presence of a crystalline metallic aluminosilicate having uniform large pore openings of about 6 to 15 Angstrom units is described in U.S. Pat. No. 2,290,607 (Lavaud). U.S. Pat. No. 3,251,897 (Wise) describes alkylation of aromatic hydrocarbons in the presence of X- or Y-type crystalline aluminosilicate zeolites, specifically such large pore zeolites wherein the cation is rare earth and/or hydrogen. U.S. Pat. Nos. 3,751,504 (Keown, et al.) and 3,751,506 (Burress) describe vapor phase alkylation of aromatic hydrocarbons with olefins, e.g. benzene with ethylene, in the presence of a ZSM-5 type medium pore zeolite catalyst. U.S. Pat. No. 3,755,483 (Burress) describes alkylation of aromatic hydrocarbons with olefins in the presence of a crystalline aluminosilicate zeolite material. U.S. Pat. Nos. 4,086,287 (Kaeding, et al.) and 4,117,024 (Kaeding) describe alkylation of monoalkyl benzenes with ethylene in the presence of a crystalline aluminosilicate zeolite material. U.S. Pat. No. 4,375,573 (Young) describes alkylation of mono-substituted aromatic compounds with olefins in the presence of a crystalline aluminosilicate zeolite material.

U.S. Pat. No. 4,524,230 (Haensel) describes a process for preparing alkylaromatic compounds by alkylating an aromatic material with paraffinic hydrocarbons; such as ethane, propane, n-butane, iso-butane, etc., over a catalyst having no acid activity. The paraffin material is catalytically decomposed in the presence of the nonacid-acting catalyst to give an olefin fragment which is "scavenged" by the aromatic material. The catalyst is at least one metal of Group VIII of the Periodic Table on a non-acidic solid support.

In a second method, alkylaromatic compounds are prepared by utilizing paraffinic hydrocarbons as indirect alkylating agents. U.S. Pat. Nos. 4,085,156 (Frilette, et al.) and 4,157,950 (Frilette, et al.) describe alkylation of aromatic hydrocarbons with materials derived from paraffins or cycloparaffins over a crystalline aluminosilicate zeolite characterized by a silica-to-alumina ratio of at least 10. These paraffins consist essentially of $C_6^+$ hydrocarbon which can contain significant amounts of pentane, but $C_2$–$C_4$ hydrocarbons are not present in significant amounts.

In these methods, the reactive alkylating species is usually an olefinic material, either added as part of the feed or, as in the Frilette method, generated in situ from paraffins by cracking. The cracking of the paraffin produces an olefin and a paraffin fragment of which only the olefinic fragment is effective for alkylating the aromatic compound, so that alkylation selectivity is limited to a maximum of 50 percent.

SUMMARY OF THE INVENTION

We have now found that the fundamental limitation on alkylation selectivity imposed by the cracking type mechanism disclosed by Frilette can be overcome by operating with lighter paraffins, especially propane, using mild conditions where the paraffin does not undergo a substantial degree of cracking and which are conducive to the direct alkylation of the aromatic. Because the species responsible for the alkylation is not substantially formed by cracking of the paraffin, alkylation selectivities over 50 percent may be readily achieved. The present process therefore provides a simple one-step route to the formation of alkylaromatic compounds directly from aromatics and paraffins, while increasing alkylation selectivity to at least 50 wt. percent, preferably 60 or 70 wt. percent or more, with the conversion in the 20 wt. percent to 80 wt. percent range.

According to the present invention, a mononuclear aromatic hydrocarbon is alkylated with a $C_2$–$C_4$ paraffin in the presence of an acidic zeolite catalyst in a one-step process. Because the process does not depend on significant cracking of the paraffin, the reaction products contain relatively lower amounts of alkylation products derived from cracking fragments. This behavior is in contrast with that observed with longer chain paraffins e.g. reformates, where significant quantities of short chain alkylaromatics are produced by cracking of the longer chain length paraffins. Advantageously, the reaction is conducted at elevated temperature in the presence of a crystalline metallosilicate zeolite material, such as HZSM-5.

The process can be employed to upgrade gasoline fractions by reducing benzene concentration, generating more volume of gasoline, reducing gasoline density, and improving octane quality. In the petrochemicals manufacturing industry, the process affords an economical approach to producing alkylated aromatic materials from simple starting materials, such as benzene and propane. Hydrogen is not required in the process, eliminating costly hydrogen recirculation.

In a preferred embodiment, a mixed feed consisting essentially of paraffin and aromatic hydrocarbon is conveyed through a catalytic fixed bed containing an acid zeolite catalyst. The reaction can be operated in a continuous fashion or batchwise.

DESCRIPTION OF PREFERRED EMBODIMENTS

An aromatic feedstock containing predominantly mononuclear aromatics such as benzene, toluene or mixtures of these compounds is co-fed to a catalytic fixed bed reactor in combination with a stream of a low molecular weight $C_2$–$C_4$ paraffin; such as ethane, propane, isobutane, n-butane or mixtures thereof. The weight hourly space velocity (WHSV) of the combined feeds is in a range from about 0.1–5.0 based on active catalyst, and the temperature and pressure conditions are generally mild as compared to cracking conditions. Preferred temperature is in that range from about 315°–480° C. (600°–900° F.), and pressure varies from about 2850 to 13750 kPa (400–2000 psig).

As the combined reactants pass through the fixed bed of alkylation catalyst in a continuous fashion, the low molecular weight paraffin material alkylates the aromatic component of the feed directly. In the presence of an alkylatable mononuclear moiety, such as benzene or toluene, the paraffin material combines freely to produce aromatic materials having saturated lower aliphatic side-chains. Examples of such products are $C_7$–$C_{10}$ methyl ethyl benzenes, propyl benzenes, and some naphthalenes. If toluene is the feedstock, a similar range of products is formed.

It is believed that the conditions employed are conducive to the dehydrogenation of the paraffin to form an olefin intermediate which then functions as the effective alkylating agent. Unlike the case with longer chain paraffins e.g. $C_6$ paraffins, reformates etc., relatively little cracking occurs so that most of the paraffin is available to react through the intermediate with the aromatic compound; in this way high alkylation selectivity is readily attainable. Thus, the reaction is believed to proceed through sequential dehydrogenation and alkylation steps with some isomerization and disproportionation (accounting for the presence of some methyl-substituted aromatics in the product).

The alkylation of the aromatic feed is preferably conducted in the absence of added hydrogen, as this is detrimental to the reaction. In the presence of hydrogen, side reactions, such as hydrocracking, are possible. The hydrogen content of the reaction mixture typically is less than two moles per mole of hydrocarbon.

Since the reaction proceeds efficiently without the presence of any unsaturated hydrocarbons, the reaction mixture can be substantially free of added olefin, although some olefin impurity is present in commercial feedstocks. In a preferred embodiment, the reaction mixture consists essentially of at least one benzenoid compound and propane in a weight ratio of 10:1 to 1:10.

Products generated with a high selectivity during the reaction are the alkylated forms of mononuclear aromatic hydrocarbons. Although generally of less commercial interest, the products of reactive intermediates would also react with condensed rings, such as naphthalene or methyl naphthalene.

When butane is used as a fraction of the mixed feed, either the normal or iso- form or mixtures can be employed, as isomerization of the butane occurs under the reaction conditions.

A significant amount of naphthalenes may be formed as products during the reaction (see Examples) because of hydrogen transfer and disproportionation of reactive alkylated aromatics.

Catalysts employed in the fixed bed alkylation reactor are porous siliceous acid zeolite materials. Preferred zeolites are ZSM-5, ZSM-11, ZSM-22, ZSM-23, ZSM-35, ZSM-38, ZSM-45, ZSM-48, and/or ZSM-50 and mixtures thereof. Although medium pore metallosilicate zeolites are preferred, it is possible to employ larger pore zeolites, such as ZSM-12, zeolite beta, ZSM-20 and siliceous zeolites with the faujasite structure. In a most preferred example, the catalyst is a crystalline aluminosilicate HZSM-5 zeolite material.

The preferred crystalline aluminosilicate zeolites have a silica to alumina molar ratio of at least 12, a constraint index of about 1 to 12 and acid cracking activity of about 50–1000. Representative aluminosilicates having a ZSM-5 structure are ZSM-5, ZSM-11, ZSM-22, ZSM-23, ZSM-35 and ZSM-38. ZSM-5 is disclosed and claimed in U.S. Pat. No. 3,702,886 (Argauer et al); ZSM-11 is disclosed and claimed in U.S. Pat. No. 3,709,979 (Chu). Also, see U.S. Pat. No. 3,832,449 (Rosinski, et al.) for ZSM-12; U.S. Pat. No. 4,076,842 (Rubin, et al.) for ZSM-23; U.S. Pat. No. 4,016,245 (Plank, et al.) for ZSM-35; U.S. Pat. No. 4,046,839 (Papetti) for ZSM-38. The disclosures of these patents are incorporated herein by reference. A suitable shape selective medium pore catalyst for fixed bed is a small crystal H-ZSM-5 zeolite (silica:alumina ratio =40:1) with alumina binder in the form of cylindrical extrudates of about 1–5 mm. Other pentasil catalysts which may be used include a variety of medium pore (5 to 8 Angstrom) siliceous materials; such as zeolite beta, gallo-silicates, ferrosilicates, and/or aluminosilicates disclosed in U.S. Pat. Nos. 4,414,413 (Sitzmann, et al.) and 4,417,088 (Miller) and 3,308,069 (Reissue 28,341) (Wadlinger, et al.), incorporated herein by reference. Catalysts can have a crystalline size of about 0.02 to 1.0 microns.

The members of the class of zeolites useful herein have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 Angstroms. On the other hand, zeolites which provide relatively free access to the internal zeolite structure have a low value for the Constraint Index, and usually pores of large size, e.g. greater than 8 Angstroms. The method by which Constraint Index is determined is described fully in U.S. Pat. No. 4,016,218 (Haag, et al.), incorporated herein by reference for details of the method.

Constraint Index (CI) values for some typical materials are:

|  | CI | (at test temperature) |
| --- | --- | --- |
| ZSM-4 | 0.5 | (316° C.) |
| ZSM-5 | 6-8.3 | (371° C.-316° C.) |
| ZSM-11 | 5-8.7 | (371° C.-316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6-2.0 | (316° C.-399° C.) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables, such as the crystal size of the zeolite, the presence of possibly occluded contaminants and binders intimately combined with the zeolite, may affect the CI. It will, accordingly, be understood by those skilled in the art that the CI, as utilized herein, while affording a highly useful means for characterizing the zeolites of interest, is approximate, taking into consideration the manner of its determination, with the possibility, in some instances, of compounding variable extremes. However, in all instances, at a temperature within the above-specified range of 290° C. to about 538° C., the CI will have a value any given zeolite of interest herein within the approximate range of 1 to 12.

The crystalline metallosilicate zeolite catalyst employed in the invention is preferably in the acid form. However, the acid sites on the catalyst can be partially ion-exchanged with metals. Suitable metal cations for exchange include Groups I through VIII of the Periodic Table, including, by way of example, nickel, copper, zinc, palladium, calcium or rare earth metals. Such promoters may be incorporated with the zeolite in accordance with the ion exchange technique or by other techniques such as impregnation.

EXAMPLE 1

A mixture of benzene and propane in a weight ratio of about 1:1 was fed continuously to a fixed bed isothermal tubular catalytic reactor. The bed is packed with an H-ZSM-5 aluminosilicate catalyst of silica to alumina ratio equal to 40, and having a crystal size of 0.02-0.05 microns. The acid cracking (alpha) value of the catalyst is 513.

The reaction was conducted at a temperature of 385°-399° C. (725°-750° F.) and a pressure of 6,184 kPa (900 psig) and in the absence of hydrogen. The weight hourly space velocity (WHSV) of the feed is 2.1-2.2; and the continuous operation proceeds for 8 days.

Products are analyzed at regular intervals to determine the amount of feed conversion and the product distribution. The following table illustrates the effectiveness of the reaction for alkylating aromatic materials with paraffins:

TABLE 1

| Charge (wt. %) | | | | | |
| --- | --- | --- | --- | --- | --- |
| Propane | 35 | 36 | 34 | 36 | 36 |
| Benzene | 65 | 64 | 66 | 64 | 64 |
| Time on Stream (hrs.) | 49 | 121 | 145 | 173 | 193 |
| Temperature (°C.) | 385 | 385 | 399 | 399 | 399 |
| Pressure (kPa) | 6183 | 6183 | 6183 | 6183 | 6183 |
| Catalyst Type HZSM-5 ($SiO_2/Al_2O_3$ = 40, $\alpha$ = 513) | | | | | |
| Product formed | wt. % | wt. % | wt. % | wt. % | wt. % |
| $C_1$ | 2.07 | 2.07 | 3.21 | 2.75 | 2.80 |
| $C_2$ | 1.45 | 1.43 | 3.07 | 2.79 | 2.59 |
| Iso-$C_4$ | 0.73 | 0.69 | 1.19 | 1.14 | 1.15 |
| N—$C_4$ | 1.04 | 1.06 | 1.46 | 1.48 | 1.54 |
| Iso-$C_5$ | 0.08 | 0.08 | 0.15 | 0.14 | 0.14 |
| N—$C_5$ | 0.06 | 0.06 | 0.10 | 0.10 | 0.10 |
| 2-M—$C_5$ | 0.01 | 0.01 | 0.01 | 0.01 | 0.01 |
| 3-M—$C_5$ | 0.00 | 0.00 | 0.01 | 0.01 | 0.01 |
| N—$C_6$ | 0.01 | 0.01 | 0.01 | 0.01 | 0.01 |
| $C_{13+}$ | 0.30 | 0.24 | 0.58 | 0.54 | 0.48 |
| benzene (starting material) | 36.19 | 44.86 | 43.86 | 33.86 | 35.39 |
| propane (starting material) | 19.33 | 23.75 | 26.78 | 18.03 | 18.71 |
| toluene | 9.92 | 8.48 | 18.71 | 17.50 | 16.75 |
| $C_8$ aromatics | 11.86 | 11.24 | 13.24 | 13.00 | 12.78 |
| $C_9$ aromatics | 2.27 | 2.55 | 4.31 | 4.10 | 3.92 |
| $C_{10}$ mononuclear aromatics | 1.56 | 1.11 | 1.02 | 1.70 | 1.62 |
| $C_{11}$-$C_{12}$ mononuclear aromatics | 0.25 | 0.22 | 0.44 | 0.40 | 0.36 |
| Naphthalene | 0.23 | 0.19 | 0.32 | 0.30 | 0.28 |
| Total Wt. % Conversion | 31.39 | 29.36 | 48.52 | 45.90 | 44.48 |
| Wt. % $C_3H_8$ Conversion | 32.39 | 25.53 | 46.80 | 48.46 | 46.50 |
| Wt. % $C_6H_6$ Conversion | 30.85 | 31.51 | 49.39 | 44.44 | 43.34 |
| Wt. % Selectivity | | | | | |
| $C_1$-$C_2$ | 11.21 | 11.92 | 12.94 | 12.07 | 12.13 |
| $C_4$ | 5.64 | 5.96 | 5.46 | 5.71 | 6.05 |
| $C_5$-$C_6$ | 0.51 | 0.55 | 0.57 | 0.59 | 0.61 |
| $C_{7+}$ aromatics | 82.63 | 81.54 | 81.00 | 81.61 | 81.23 |

EXAMPLE 2

A mixture of benzene and propane in a weight ratio of about 1:1 was fed continuously to a fixed bed isothermal tubular catalytic reactor. The bed is packed with an H-ZSM-12 aluminosilicate catalyst of silica-to-alumina ratio equal to 76. The acid cracking (alpha) value of the catalyst is 160.

The reaction conditions are given in Table 2. The weight hourly space velocity (WHSV) of the feed is 3.1–3.3. Products were analyzed to determine the amount of feed conversion and the product distribution.

TABLE 2

| Charge (wt. %) | | |
|---|---|---|
| Propane | 50.6 | 53.1 |
| Benzene | 49.3 | 46.7 |
| Time on Stream (hrs.) | 4.8 | 2.3 |
| Temperature (°C.) | 453 | 481 |
| Pressure (kPa) | 5497 | 5497 |
| Catalyst Type HZSM-12 ($SiO_2/Al_2O_3$ = 76, $\alpha$ = 160) | | |
| WHSV | | |

| Product formed | wt. % | wt. % |
|---|---|---|
| $C_1$ | 0.43 | 1.12 |
| $C_2$ | 0.28 | 0.86 |
| Iso-$C_4$ | 0.64 | 1.23 |
| N—$C_4$ | 0.90 | 1.80 |
| Iso-$C_5$ | 0.08 | 0.16 |
| N—$C_5$ | 0.07 | 0.14 |
| 2-M—$C_5$ | 0.03 | 0.03 |
| 3-M—$C_5$ | 0.01 | 0.02 |
| N—$C_6$ | 0.03 | 0.03 |
| *$C_{13+}$ | 0.15 | 0.44 |
| benzene (starting material) | 35.26 | 27.67 |
| propane (starting material) | 47.16 | 42.02 |
| toluene | 7.03 | 12.74 |
| $C_8$ aromatics | 4.03 | 5.57 |
| $C_9$ aromatics | 1.8 | 2.08 |
| $C_{10}$ mononuclear aromatics | 0.54 | 0.87 |
| $C_{11}$-$C_{12}$ | 0.07 | 0.06 |
| mononuclear aromatics | 0.57 | 1.08 |
| Naphthalene | 0.90 | 2.03 |
| *M—Naphthalenes | | |
| Total Wt. % Conversion | 17.58 | 30.30 |
| Wt. % $C_3H_8$ Conversion | 6.72 | 20.88 |
| Wt. % $C_6H_6$ Conversion | 28.46 | 40.79 |
| Wt. % Selectivity | | |
| $C_1$-$C_2$ | 4.04 | 6.53 |
| $C_4$ | 8.76 | 10.00 |
| $C_5$-$C_6$ | 1.25 | 1.32 |
| $C_7$+ aromatics | 85.84 | 82.08 |

*Approximate Analysis

EXAMPLE 3

A mixture of benzene and propane in a weight ratio of about 1:1 was fed continuously to a fixed bed isothermal tubular catalytic reactor. The bed is packed with an H-ZSM-23 aluminosilicate catalyst of silica-to-alumina ratio equal to 100. The acid cracking (alpha) value of the catalyst is 47.

The reaction conditions are give in Table 3. The weight hourly space velocity (WHSV) of the feed is 3–3.1 and no hydrogen is present.

Products were analyzed to determine the amount of feed conversion and the product distribution. The following table illustrates the effectiveness of the reaction for alkylating aromatic materials with paraffins:

TABLE 3

| Charge (wt. %) | | |
|---|---|---|
| Propane | 50.3 | 50.8 |
| Benzene | 49.6 | 49 |
| Time on Stream (hrs.) | 5.5 | 28.8 |
| Temperature (°C.) | 455 | 482 |
| Pressure (kPa) | 5497 | 5497 |
| Catalyst Type HZSM-23 ($SiO_2/Al_2O_3$ = 100, $\alpha$ = 47) | | |

| Product formed | wt. % | wt. % |
|---|---|---|
| $C_1$ | 2.75 | 4.16 |
| $C_2$ | 1.41 | 2.55 |
| Iso-$C_4$ | 0.35 | 0.66 |
| N—$C_4$ | 0.60 | 1.22 |
| Iso-$C_5$ | 0.06 | 0.13 |

TABLE 3-continued

| N—$C_5$ | 0.10 | 0.16 |
|---|---|---|
| 2-M—$C_5$ | 0.03 | 0.04 |
| 3-M—$C_5$ | 0.01 | 0.02 |
| N—$C_6$ | 0.03 | 0.04 |
| *$C_{13+}$ | 0.01 | 0.04 |
| benzene (starting material) | 36.08 | 32.07 |
| propane (starting material) | 38.49 | 32.54 |
| toluene | 0.80 | 2.41 |
| $C_8$ aromatics | 13.42 | 15.76 |
| $C_9$ aromatics | 3.16 | 3.56 |
| $C_{10}$ mononuclear aromatics | 1.92 | 2.90 |
| $C_{11}$-$C_{12}$ | | |
| mononuclear aromatics | 0.27 | 0.28 |
| Naphthalene | 0.05 | 0.15 |
| *M—Naphthalenes | 0.4 | 0.93 |
| Total Wt. % Conversion | 25.4 | 35.23 |
| Wt. % $C_3H_8$ Conversion | 23.42 | 35.97 |
| Wt. % $C_6H_6$ Conversion | 27.24 | 34.58 |
| Wt. % Selectivity | | |
| $C_1$-$C_2$ | 16.38 | 19.05 |
| $C_4$ | 3.78 | 3.66 |
| $C_5$-$C_6$ | 1.10 | 1.36 |
| $C_7$+ aromatics | 78.86 | 73.89 |

*Approximate Analysis

EXAMPLE 4

A mixture of benzene and propane in a weight ratio of about 1:1 was fed continuously to a fixed bed isothermal tubular catalytic reactor. The bed is packed with an H-ZSM-11 aluminosilicate catalyst of silica-to-alumina ratio equal to 70.

The reaction conditions are given in Table 4. The weight hourly space velocity (WHSV) of the feed is 2.8–3.2 and the continuous operation is conducted in the absence of hydrogen.

TABLE 4

| Charge (wt. %) | | |
|---|---|---|
| Propane | 49.6 | 46 |
| Benzene | 50.2 | 53.9 |
| Time on Stream (hrs.) | 22.8 | 46.8 |
| Temperature (°C.) | 427 | 454 |
| Pressure (kPa) | 5497 | 5497 |
| Catalyst Type HZSM-11 ($SiO_2/Al_2O_3$ = 70, $\alpha$ = 102) | | |

| Product formed | wt. % | wt. % |
|---|---|---|
| $C_1$ | .93 | 2.66 |
| $C_2$ | .33 | 2.5 |
| Iso-$C_4$ | .34 | 1.46 |
| N—$C_4$ | .5 | 2.07 |
| Iso-$C_5$ | .03 | .17 |
| N—$C_5$ | .04 | .15 |
| 2-M—$C_5$ | .01 | .02 |
| 3-M—$C_5$ | .01 | .01 |
| N—$C_6$ | .01 | .02 |
| *$C_{13+}$ | 0 | .02 |
| benzene (starting material) | 44.06 | 31.52 |
| propane (starting material) | 42.07 | 27.48 |
| toluene | 2.33 | 14.59 |
| $C_8$ aromatics | 7.04 | 10.34 |
| $C_9$ aromatics | 1.41 | 3.43 |
| $C_{10}$ mononuclear aromatics | .48 | 1.74 |
| $C_{11}$-$C_{12}$ | .03 | .23 |
| mononuclear aromatics | | |
| Naphthalene | .15 | .4 |
| *M—Naphthalenes | .22 | 1.15 |
| Total Wt. % Conversion | 13.87 | 41 |
| Wt. % $C_3H_8$ Conversion | 15.23 | 40.26 |
| Wt. % $C_6H_6$ Conversion | 12.25 | 41.48 |
| Wt. % Selectivity | | |
| $C_1$-$C_2$ | 9.08 | 12.59 |
| $C_4$ | 6.06 | 8.61 |
| $C_5$-$C_6$ | .72 | .93 |
| $C_7$+ aromatics | 84.07 | 77.8 |

*Approximate Analysis

EXAMPLE 5

A mixture of benzene and propane in a weight ratio of about 1:1 was fed continuously to a fixed bed isothermal tubular catalytic reactor. The bed is packed with an aluminosilicate catalyst (Zeolite Beta, disclosed in U.S. Pat. No. 3,308,069) of silica-to-alumina ratio equal to 40. The reaction conditions are given in Table 5. The weight hourly space velocity (WHSV) of the feed is 2.8-3.3 and the continuous operation is conducted in the absence of hydrogen.

TABLE 5

| Charge (wt. %) | | | |
|---|---|---|---|
| Propane | 52.39 | 54.74 | 51.69 |
| Benzene | 47.45 | 45.08 | 48.16 |
| Time on Stream (hrs.) | 5 | 5.3 | 5 |
| Temperature (°C.) | 398 | 453 | 468 |
| Pressure (kPa) | 5497 | 5497 | 5497 |
| Catalyst Type: Zeolite Beta ($SiO_2/Al_2O_3 = 40$) | | | |
| Product formed | wt. % | wt. % | wt. % |
| $C_1$ | 0 | 0 | .25 |
| $C_2$ | 0 | 0 | .24 |
| Iso-$C_4$ | .45 | .57 | .70 |
| N—$C_4$ | .23 | .5 | .6 |
| Iso-$C_5$ | .06 | .08 | .09 |
| N—$C_5$ | .03 | .05 | .06 |
| 2-M—$C_5$ | .02 | .02 | .02 |
| 3-M—$C_5$ | .01 | .01 | .01 |
| N—$C_6$ | .01 | .02 | .02 |
| $C_{13+}$ | .12 | .13 | .34 |
| benzene (starting material) | 40.75 | 36.58 | 35.34 |
| propane (starting material) | 48.35 | 49.72 | 46.14 |
| toluene | 4.43 | 6.24 | 8.55 |
| $C_8$ aromatics | 2.87 | 2.95 | 3.52 |
| $C_9$ aromatics | 1.48 | 1.37 | 1.44 |
| $C_{10}$ mononuclear aromatics | 0.29 | .32 | .42 |
| $C_{11}$-$C_{12}$ mononuclear aromatics | .02 | .03 | .02 |
| Naphthalene | .34 | .59 | .94 |
| M-Naphthalenes | .54 | .79 | 1.27 |
| Total Wt. % Conversion | 10.91 | 13.7 | 18.5 |
| Wt. % $C_3H_8$ Conversion | 7.7 | 9.17 | 10.74 |
| Wt. % $C_6H_6$ Conversion | 14.12 | 18.86 | 26.62 |
| Wt. % Selectivity | | | |
| $C_1$-$C_2$ | 0 | 0 | 2.65 |
| $C_4$ | 6.23 | 7.81 | 17.02 |
| $C_5$-$C_6$ | 1.19 | 1.31 | 1.13 |
| $C_7$ + aromatics | 92.08 | 90.66 | 89.09 |

EXAMPLE 6

A mixture of benzene and ethane in a weight ratio of about 1:1 was fed continuously to a fixed bed isothermal tubular catalytic reactor. The bed is packed with an H-ZSM-5 aluminosilicate catalyst of silica-to-alumina ratio equal to 40. The acid cracking (alpha) value of the catalyst is 500.

The reaction conditions are given in Table 6. The weight hourly space velocity (WHSV) of the feed is 2.9-3.3 and the continuous operation is conducted in the absence of hydrogen.

TABLE 6

| Charge (wt. %) | | |
|---|---|---|
| Ethane | 47.93 | 49.94 |
| Benzene | 52.07 | 50.06 |
| Time on Stream (hrs.) | 52.8 | 4.8 |
| Temperature (°C.) | 454 | 454 |
| Pressure (kPa) | 5497 | 5497 |
| Catalyst Type H-ZSM-5 $SiO_2/Al_2O_3 = 40$, $\alpha = 500$) | | |
| Product formed | wt. % | wt. % |
| $C_1$ | 0 | 0 |
| $C_2$ (starting material) | 44.89 | 45.24 |
| propane | 0 | 0 |
| Iso-$C_4$ | 0 | 0 |
| N—$C_4$ | 0 | 0 |
| Iso-$C_5$ | 0 | 0 |
| N—$C_5$ | 0 | 0 |
| 2-M—$C_5$ | 0 | 0 |
| 3-M—$C_5$ | 0 | 0 |
| N—$C_6$ | 0 | 0 |
| $C_{13+}$ | .01 | .03 |
| benzene (starting material) | 47.76 | 48.99 |
| toluene | 5.27 | 3.82 |
| $C_8$ aromatics | 1.01 | .95 |
| $C_9$ aromatics | .07 | .05 |
| $C_{10}$ mononuclear aromatics | .02 | .01 |
| $C_{11}$-$C_{12}$ mononuclear aromatics | 0 | 0 |
| Naphthalene | .57 | .49 |
| M-Naphthalenes | .41 | .4 |
| Total Wt. % Conversion | 7.36 | 5.76 |
| Wt. % $C_2H_6$ Conversion | 6.34 | 9.41 |
| Wt. % $C_6H_6$ Conversion | 8.28 | 2.14 |

EXAMPLE 7

A mixture of benzene and n-butane in a weight ratio of about 1:1 was fed continuously to a fixed bed isothermal tubular catalytic reactor. The bed is packed with an H-ZSM-5 aluminosilicate catalyst of silica-to-alumina ratio equal to 40. The acid cracking (alpha) value of the catalyst is 500.

The reaction conditions are given in Table 7. The weight hourly space velocity (WHSV) of the feed is 2.9-3.1 and the continuous operation is conducted in the absence of hydrogen.

TABLE 7

| Charge (wt. %) | | | | | |
|---|---|---|---|---|---|
| n-butane | 49.11 | 50.8 | 50.9 | 53 | 51 |
| Benzene | 50.9 | 49.2 | 49.1 | 47 | 49 |
| Time on Stream (hrs.) | 4.8 | 28.8 | 52.8 | 73.5 | 97.5 |
| Temperature (°C.) | 371 | 343 | 316 | 399 | 398 |
| Pressure (kPa) | 5497 | 5497 | 5497 | 5497 | 1374 |
| Catalyst Type H-ZSM-5 ($SiO_2/Al_2O_3 = 40$, $\alpha = 500$) | | | | | |
| Product formed | wt. % | wt. % | wt. % | wt. % | wt. % |
| $C_1$ | .88 | .3 | .06 | 1.55 | .46 |
| $C_2$ | 2.26 | .73 | .38 | 4.76 | 1.61 |
| propane | 25.88 | 27.43 | 2.88 | 24.9 | 30.8 |
| Iso-$C_4$ | 2.87 | 4.86 | 3.52 | 2.37 | 3.07 |
| N—$C_4$ (starting material) | 3.08 | 6.07 | 40.23 | 2.92 | 3.2 |
| Iso-$C_5$ | .66 | 1.49 | .59 | .59 | .61 |
| N—$C_5$ | .32 | .74 | 1.05 | .65 | .26 |
| 2-M—$C_5$ | .06 | .16 | .08 | .05 | .05 |
| 3-M—$C_5$ | .04 | .11 | .04 | .04 | .03 |
| N—$C_6$ | .03 | .09 | .12 | .04 | .03 |
| $C_{13+}$ | .25 | .26 | .01 | .32 | .19 |
| benzene (starting material) | 19.16 | 28.09 | 46.37 | 8.57 | 20.85 |
| toluene | 18.55 | 9.1 | .27 | 19.17 | 17.19 |
| $C_8$ aromatics | 13.84 | 9.49 | 1.68 | 17.3 | 11.77 |
| $C_9$ aromatics | 5.89 | 5.63 | 1.69 | 7.63 | 4.25 |
| $C_{10}$ mononuclear aromatics | 3.03 | 3.35 | .9 | 4.2 | 2.65 |
| $C_{11}$-$C_{12}$ mononuclear aromatics | .53 | .83 | .08 | .84 | .57 |
| Naphthalene | .32 | .1 | 0 | .54 | .42 |
| *M-Naphthalenes | 2.28 | 1.02 | .04 | 3.47 | 1.92 |
| Total Wt. % Conversion | 77.75 | 65.84 | 13.4 | 88.51 | 75.92 |
| Wt. % N—$C_4$ Conversion | 93.73 | 88.05 | 21.02 | 94.49 | 93.6 |
| Wt. % $C_6H_6$ Conversion | 62.35 | 42.92 | 5.48 | 81.78 | 57.88 |
| Wt. % Selectivity | | | | | |
| $C_1$-$C_2$ | 4.04 | 1.56 | 3.28 | 7.13 | 2.73 |
| $C_3$ | 33.29 | 41.66 | 21.49 | 28.13 | 40.56 |
| Iso-$C_4$ + $C_5$ + $C_6$ | 5.16 | 11.42 | 40.3 | 4.27 | 5.39 |

TABLE 7-continued

| | | | | | |
|---|---|---|---|---|---|
| $C_7$ + aromatics | 57.48 | 45.23 | 34.85 | 60.41 | 51.32 |

*Approximate Analysis

EXAMPLE 8

A mixture of toluene and propane in a weight ratio of about 5:1 to 2:1 was fed continuously to a fixed bed isothermal tubular catalytic reactor. The bed is packed with an H-ZSM-5 aluminosilicate catalyst of silica-to-alumina ratio equal to 40. The acid cracking (alpha) value of the catalyst is 500.

The reaction conditions are given in Table 8. The weight hourly space velocity (WHSV) of the feed is 2.9–3.6 and the continuous operation is conducted in the absence of hydrogen.

EXAMPLE 9

A mixture of benzene and propane in a weight ratio of about 2:1 to 5:1 was fed continuously to a fixed bed isothermal tubular catalytic reactor. The bed is packed with an H-ZSM-5 aluminosilicate catalyst of silica-to-alumina ratio equal to 40. The acid cracking (alpha) value of the catalyst is 500.

The reaction conditions are given in Table 9. The weight hourly space velocity (WHSV) of the feed is 2.8–3.0 and the continuous operation is conducted in the absence of hydrogen.

TABLE 8

| Charge (wt. %) | | | | | | | | | |
|---|---|---|---|---|---|---|---|---|---|
| Propane | 50.6 | 51.1 | 54.1 | 50 | 51 | 46 | 50 | 67.2 | 35.7 |
| Toluene | 49.3 | 48.8 | 45.7 | 50 | 49 | 52 | 50 | 32.6 | 64.3 |
| Time on Stream (hrs.) | 4.7 | 28.8 | 52.8 | 173 | 120 | 215 | 219 | 239 | 263 |
| Temperature (°C.) | 399 | 371 | 426 | 426 | 426 | 426 | 440 | 440 | 440 |
| Pressure (kPa) | 5497 | 5497 | 5497 | 5497 | 5497 | 5497 | 5497 | 5497 | 5497 |

Catalyst Type H-ZSM-5 ($SiO_2Al_2O_3$ = 40, α = 500)

| Product formed | wt. % | wt. % | wt. % | wt. % | wt. % | wt. % | wt. % | wt. % | wt. % |
|---|---|---|---|---|---|---|---|---|---|
| $C_1$ | 2.53 | .89 | 4.2 | 2.76 | 2.53 | 2.45 | 3.24 | 3.28 | 2.03 |
| $C_2$ | 5.37 | 1.09 | 8.79 | 5.89 | 5.1 | 4.8 | 7.1 | 7.1 | 3.8 |
| Iso-$C_4$ | 2.48 | 1.04 | 2.18 | 2.61 | 2.46 | 2.39 | 2.25 | 3.35 | 1.38 |
| N-$C_4$ | 3.21 | 1.57 | 2.89 | 3.59 | 3.32 | 3.25 | 3.06 | 4.75 | 1.92 |
| Iso-$C_5$ | .61 | .09 | .54 | .7 | .61 | .61 | .57 | .91 | .31 |
| N-$C_5$ | .34 | .08 | .34 | .45 | .38 | .4 | .35 | .61 | .19 |
| 2-M-$C_5$ | .05 | .02 | .05 | .07 | .06 | .06 | .06 | .1 | .03 |
| 3-M-$C_5$ | .03 | .01 | .03 | .04 | .04 | .04 | .04 | .06 | .02 |
| N-$C_6$ | .07 | .02 | .04 | .05 | .05 | .05 | .05 | .08 | .02 |
| $C_{13}$ + | .08 | .01 | .11 | .02 | .01 | .01 | .02 | 0 | .01 |
| benzene | 4.84 | 7.83 | 3.98 | 4.48 | 5.15 | 5.19 | 4.76 | 2.99 | 8.44 |
| propane (starting material) | 29.36 | 42.69 | 24.95 | 30.53 | 29.71 | 29.96 | 26.54 | 39.02 | 18.88 |
| toluene (starting material) | 17.07 | 21.37 | 15.42 | 16.2 | 17.45 | 17.85 | 17.03 | 11.88 | 24.75 |
| $C_8$ aromatics | 18.4 | 15.52 | 18.21 | 18.18 | 18.97 | 19.12 | 19.17 | 14.08 | 23.57 |
| $C_9$ aromatics | 8.57 | 5.32 | 8.64 | 8.11 | 8.2 | 8.16 | 8.33 | 6.38 | 8.82 |
| $C_{10}$ mononuclear aromatics | 3.93 | 1.91 | 4.31 | 3.56 | 3.47 | 3.39 | 3.57 | 2.74 | 3.29 |
| $C_{11}$-$C_{12}$ mononuclear aromatics | .45 | .11 | .87 | .37 | .53 | .49 | .60 | .30 | .40 |
| Naphthalene | .22 | .04 | .5 | .3 | .28 | .25 | 5 | .33 | .35 |
| *M-Naphthalenes | 2.3 | .37 | 3.84 | 1.98 | 1.59 | 1.42 | 2.65 | 1.85 | 1.77 |
| Total Wt. % Conversion | 53.57 | 35.94 | 59.63 | 53.27 | 52.85 | 52.19 | 56.43 | 49.1 | 56.35 |
| Wt. % $C_3H_8$ Conversion | 41.95 | 16.39 | 53.88 | 38.89 | 41.81 | 37.05 | 46.88 | 41.9 | 47.04 |
| Wt. % Toluene Conversion | 65.37 | 56.19 | 66.28 | 67.52 | 64.23 | 65.85 | 65.86 | 63.59 | 61.48 |
| Wt. % Selectivity | | | | | | | | | |
| $C_1$-$C_2$ | 14.75 | 5.51 | 21.78 | 16.24 | 14.44 | 13.89 | 18.29 | 21.12 | 10.27 |
| $C_4$ | 10.62 | 7.26 | 8.5 | 11.64 | 10.94 | 10.81 | 9.41 | 16.5 | 5.85 |
| $C_5$-$C_6$ | 2.1 | .61 | 1.78 | 2.57 | 2.27 | 2.32 | 2 | 3.83 | 1.05 |
| $C_6$+ aromatics | 72.41 | 86.56 | 67.85 | 69.46 | 72.28 | 72.87 | 70.18 | 58.39 | 82.74 |

*Approximate Analysis

TABLE 9

| Charge (wt. %) | | | | |
|---|---|---|---|---|
| Propane | 34.3 | 51.2 | 65.8 | 49.1 |
| Benzene | 65.6 | 48.6 | 34.1 | 49.1 |
| Time on Stream (hrs.) | 5.2 | 5.3 | 5.2 | 5.2 |
| Temperature (°C.) | 455 | 453 | 455 | 426 |
| Pressure (kPa) | 5497 | 5497 | 5497 | 5497 |

Catalyst Type H-ZSM-5 ($SiO_2/Al_2O_3$ = 40, α-value = 500)

| Product formed | wt. % | wt. % | wt. % | wt. % |
|---|---|---|---|---|
| $C_1$ | 7.23 | 7.9 | 9.29 | 5.73 |
| $C_2$ | 9.99 | 13.23 | 18.47 | 9.42 |
| Iso-$C_4$ | .25 | .66 | 1.48 | 1.21 |
| N-$C_4$ | .33 | .89 | 1.94 | 1.62 |
| Iso-$C_5$ | .03 | .08 | .18 | .17 |
| N-$C_5$ | .02 | .06 | .14 | .12 |
| 2-M-$C_5$ | 0 | .01 | .03 | 0 |
| 3-M-$C_5$ | 0 | .01 | .02 | .02 |
| N-$C_6$ | 0 | .01 | .02 | .01 |
| *$C_{13}$+ | .44 | .46 | .35 | .22 |
| benzene (starting material) | 14.21 | 9.25 | 4.31 | 9.99 |
| propane (starting material) | 4.32 | 9.92 | 20.27 | 16.41 |
| toluene | 27.84 | 22 | 12.87 | 22.33 |
| $C_8$ aromatics | 19.13 | 17.82 | 12.84 | 18.29 |
| $C_9$ aromatics | 5.52 | 6.17 | 5.43 | 6.73 |
| $C_{10}$ mononuclear aromatics | 2.32 | 2.93 | 2.99 | 3.25 |
| $C_{11}$-$C_{12}$ mononuclear aromatics | .16 | .58 | .77 | .53 |
| Naphthalene | 1.65 | 1.32 | 1.2 | .59 |
| *M-Naphthalenes | 6.56 | 6.68 | 7.33 | 3.3 |
| Total Wt. % Conversion | 81.47 | 80.83 | 75.43 | 73.59 |
| Wt. % $C_3H_8$ Conversion | 87.41 | 80.63 | 69.17 | 66.55 |
| Wt. % $C_6H_6$ Conversion | 78.34 | 80.98 | 87.35 | 80.33 |
| Wt. % Selectivity | | | | |
| $C_1$-$C_2$ | 21.14 | 26.14 | 36.8 | 20.59 |
| $C_4$ | .71 | 1.92 | 4.55 | 3.85 |
| $C_5$-$C_6$ | .06 | .21 | .56 | .48 |

| | | | | |
|---|---|---|---|---|
| $C_7+$ aromatics | 78.09 | 71.72 | 58.04 | 75.06 |

*Approximate Analysis

EXAMPLE 10

A mixture of benzene and propane in a weight ratio of about 5:1 to 2:1 was fed continuously to a fixed bed isothermal tubular catalytic reactor. The bed is packed with an H-ZSM-5 aluminosilicate catalyst of silica-to-alumina ratio equal to 40. The acid cracking (alpha) value of the catalyst is 500.

The reaction conditions are given in Table 10. The weight hourly space velocity (WHSV) of the feed is 2.9–3.1 and the continuous operation is conducted in the absence of hydrogen.

TABLE 10

| Charge (wt. %) | | | | |
|---|---|---|---|---|
| Propane | 49.1 | 50.8 | 33.9 | 67.5 |
| Benzene | 50.8 | 49.1 | 66 | 32.3 |
| Time on Stream (hrs.) | 5.2 | 4.8 | 5.3 | 5.2 |
| Temperature (°C.) | 426 | 399 | 397 | 399 |
| Pressure (Kpa) | 5497 | 5497 | 5497 | 5497 |
| Catalyst Type H-ZSM-5 ($SiO_2/Al_2O_3$ = 40, α-value = 500) | | | | |
| Product formed | wt. % | wt. % | wt. % | wt. % |
| $C_1$ | 5.73 | 2.06 | 1.23 | 2.40 |
| $C_2$ | 9.42 | 2.15 | .87 | 3.24 |
| Iso-$C_4$ | 1.21 | 1.64 | .44 | 2.9 |
| N—$C_4$ | 1.62 | 2.22 | .65 | 3.78 |
| Iso-$C_5$ | .17 | .18 | .04 | .51 |
| N—$C_5$ | .12 | .15 | 0 | .34 |
| 2-M-$C_5$ | 0 | .02 | .01 | .05 |
| 3-M-$C_5$ | .02 | .01 | 0 | .03 |
| N—$C_6$ | .01 | .02 | 0 | .04 |
| *$C_{13}+$ | .22 | 0 | .01 | .1 |
| benzene (starting material) | 9.99 | 30.65 | 51.53 | 17.6 |
| propane (starting material) | 16.41 | 34.99 | 24.53 | 46.13 |
| toluene | 22.33 | 10.62 | 6.23 | 10.2 |
| $C_8$ aromatics | 18.29 | 10.32 | 10.99 | 7.88 |
| $C_9$ aromatics | 6.73 | 2.93 | 1.99 | 2.84 |
| $C_{10}$ mononuclear aromatics | 3.25 | 1.35 | .81 | 1.37 |
| $C_{11}$-$C_{12}$ mononuclear aromatics | .53 | .14 | .04 | .18 |
| Naphthalene | .59 | .11 | .14 | .08 |
| *M-Naphthalenes | 3.3 | .41 | .44 | .28 |
| Total Wt. % Conversion | 73.59 | 34.36 | 23.94 | 36.27 |
| Wt. % $C_3H_8$ Conversion | 66.55 | 32.13 | 27.7 | 31.65 |
| Wt. % $C_6H_6$ Conversion | 80.33 | 37.55 | 21.89 | 45.53 |
| Wt. % Selectivity | | | | |
| $C_1$-$C_2$ | 20.59 | 12.25 | 8.77 | 15.55 |
| $C_4$ | 3.85 | 11.23 | 4.55 | 18.42 |
| $C_5$-$C_6$ | .48 | 1.11 | .38 | 2.76 |
| $C_7+$ aromatics | 75.06 | 75.32 | 86.26 | 63.22 |

EXAMPLE 11

A mixture of benzene and propane in a weight ratio of about 1:1 was fed continuously to a fixed bed isothermal tubular catalytic reactor. The bed is packed with an H-ZSM-5 aluminosilicate catalyst of silica-to-alumina ratio equal to 40. The acid cracking (alpha) value of the catalyst is 500.

The reaction conditions are given in Table 11. The weight hourly space velocity (WHSV) of the feed is 1.7–3.2 and the continuous operation is conducted in the absence of hydrogen.

TABLE 11

| Charge (wt. %) | | | | | |
|---|---|---|---|---|---|
| Propane | 50.2 | 50.4 | 52.4 | 52.7 | 53.5 |
| Benzene | 49.6 | 49.5 | 47.5 | 47.2 | 46.3 |
| Time on Stream (hrs.) | 5.4 | 28.9 | 52.9 | 76.9 | 101.2 |
| Temperature (°C.) | 426 | 426 | 440 | 454 | 440 |
| Pressure (kPa) | 2748 | 687 | 206 | 137 | 137 |
| Catalyst Type H-ZSM-5 ($SiO_2/Al_2O_3$ = 40, α-value = 500) | | | | | |
| Product formed | wt. % | wt. % | wt. % | wt. % | wt. % |
| $C_1$ | 3.51 | 1.77 | 1.52 | 2.6 | 2.7 |
| $C_2$ | 6.74 | 2.45 | 1.92 | 3.69 | 4.52 |
| Iso-$C_4$ | 1.69 | 1.27 | 1.18 | 1.23 | 1.36 |
| N—$C_4$ | 2.2 | 1.86 | 1.72 | 1.64 | 1.78 |
| Iso-$C_5$ | .23 | .12 | .1 | .09 | .12 |
| N—$C_5$ | .16 | .1 | .09 | .09 | .1 |
| 2-M-$C_5$ | .02 | .01 | .01 | .01 | .01 |
| 3-M-$C_5$ | .01 | .01 | 0 | 0 | 0 |
| N—$C_6$ | .02 | .01 | .01 | .01 | .01 |
| *$C_{13}+$ | .07 | 0 | 0 | .0 | .01 |
| benzene (starting material) | 14.16 | 34.18 | 38.54 | 35.83 | 36.89 |
| propane (starting material) | 24.63 | 36.37 | 38.7 | 35.5 | 36.8 |
| toluene | 21.9 | 11.61 | 8.27 | 9.81 | 7.59 |
| $C_8$ aromatics | 14.37 | 7.05 | 5.53 | 5.83 | 4.86 |
| $C_9$ aromatics | 4.95 | 1.72 | 1.09 | 1.23 | 1.09 |
| $C_{10}$ mononuclear aromatics | 2.35 | .78 | .59 | .71 | .54 |
| $C_{11}$-$C_{12}$ mononuclear aromatics | .37 | .1 | .02 | .03 | .02 |
| Naphthalene | .43 | .13 | .12 | .27 | .28 |
| *M-Naphthalenes | 2.15 | .43 | .32 | .82 | .96 |
| Total Wt. % Conversion | 61.21 | 29.45 | 22.6 | 28.5 | 26.2 |
| Wt. % $C_3H_8$ Conversion | 50.96 | 27.79 | 26.09 | 32.59 | 31.2 |
| Wt. % $C_6H_6$ Conversion | 71.46 | 30.91 | 18.81 | 24.04 | 20.39 |
| Wt. % Selectivity | | | | | |
| $C_1$-$C_2$ | 16.75 | 14.33 | 15.4 | 22.74 | 27.88 |
| $C_4$ | 6.34 | 10.66 | 12.88 | 10.32 | 12.28 |
| $C_5$-$C_6$ | .75 | .95 | 1.11 | .84 | 1.07 |
| $C_7+$ aromatics | 76.12 | 74.09 | 70.53 | 65.65 | 58.7 |

EXAMPLE 12

A mixture of benzene and propane in a weight ratio of about 1:1 was fed continuously to a fixed bed isothermal tubular catalytic reactor. The bed is packed with an H-ZSM-5 aluminosilicate catalyst of silica-to-alumina ratio equal to 40. The acid cracking (alpha) value of the catalyst is 500.

The reaction conditions are given in Table 12. The weight hourly space velocity (WHSV) of the feed is 3–3.1. The continuous operation is conducted in the absence of hydrogen initially and then in the presence of hydrogen.

Results given in Table 12 show the alkylation selectivity as measured by the $C_7+$ aromatics decreases when hydrogen is added to the reaction mixture due to increased hydrocracking.

TABLE 12

| Charge (wt. %) | | |
|---|---|---|
| Propane | 51.2 | 50.7 |
| Benzene | 48.6 | 49.1 |
| $H_2$/Hydrocarbon ratio | 0/1 | .4/1 |
| Time on Stream (hrs.) | 5.3 | 5.2 |
| Temperature (°C.) | 453 | 456 |
| Pressure (kPa) | 5497 | 5497 |
| Catalyst Type H-ZSM-5 ($SiO_2/Al_2O_3$ = 40, α-value = 500) | | |
| Product formed | wt. % | wt. % |
| $C_1$ | 7.9 | 10.73 |
| $C_2$ | 13.23 | 14.79 |

TABLE 12-continued

| | | |
|---|---|---|
| Iso-$C_4$ | .66 | .68 |
| N—$C_4$ | .89 | .84 |
| Iso-$C_5$ | .08 | .09 |
| N—$C_5$ | .06 | .05 |
| 2-M-$C_5$ | .01 | .01 |
| 3-M-$C_5$ | .01 | .01 |
| N—$C_6$ | .01 | 0 |
| *$C_{13+}$ | .46 | .05 |
| benzene (starting material) | 9.25 | 16.08 |
| propane (starting material) | 9.92 | 12.46 |
| toluene | 22 | 23.32 |
| $C_8$ aromatics | 17.82 | 13.64 |
| $C_9$ aromatics | 6.17 | 3.95 |
| $C_{10}$ mononuclear aromatics | 2.93 | 1.47 |
| $C_{11}$–$C_{12}$ mononuclear aromatics | .58 | .1 |
| Naphthalene | 1.32 | .4 |
| *M—Naphthalenes | 6.68 | 1.33 |
| Total Wt. % Conversion | 80.83 | 71.46 |
| Wt. % $C_3H_8$ Conversion | 80.63 | 75.45 |
| Wt. % $C_6H_6$ Conversion | 80.98 | 67.24 |
| Wt. % Selectivity | | |
| $C_1$–$C_2$ | 26.14 | 35.71 |
| $C_4$ | 1.92 | 2.13 |
| $C_5$–$C_6$ | .21 | .22 |
| $C_7$ + aromatics | 71.22 | 61.94 |

*Approximate Analysis

EXAMPLE 13

A mixture of benzene and propane in a weight ratio of about 5:1 to 2:1 was fed continuously to a fixed bed isothermal tubular catalytic reactor. The bed is packed with a gallium-substituted ZSM-5 aluminosilicate catalyst of silica-to-metal oxide ratio equal to 42. The acid cracking (alpha) value of the catalyst is 500.

The reaction conditions are given in Table 13. The weight hourly space velocity (WHSV) of the feed is 2.8–3.1 and the continuous operation is conducted in the absence of hydrogen.

TABLE 13

| Charge (wt. %) | | |
|---|---|---|
| Propane | 38.1 | 36.8 |
| Benzene | 61.8 | 63.1 |
| Time on Stream (hrs.) | 30.4 | 54.4 |
| Temperature (°C.) | 399 | 454 |
| Pressure (kPa) | 5497 | 5497 |
| Catalyst Type: [Ga] ZSM-5 | | |
| ($SiO_2/Al_2O_3$ = 521, $SiO_2/(Ga_2O_3 + Al_2O_3)$ = 42, $\alpha$-value = 500) | | |

| Product formed | wt. % | wt. % |
|---|---|---|
| $C_1$ | .41 | 4.15 |
| $C_2$ | .1 | 3.47 |
| Iso-$C_4$ | .08 | .93 |
| N—$C_4$ | .18 | 1.24 |
| Iso-$C_5$ | .01 | .12 |
| N—$C_5$ | .01 | .09 |
| 2-M-$C_5$ | 0 | .01 |
| 3-M-$C_5$ | 0 | .01 |
| N—$C_6$ | .01 | .01 |
| *$C_{13+}$ | .25 | .12 |
| benzene (starting material) | 58.04 | 29.19 |
| propane (starting material) | 33.4 | 15.12 |
| toluene | 1.45 | 21.68 |
| $C_8$ aromatics | 3.48 | 12.04 |
| $C_9$ aromatics | 2.14 | 5.33 |
| $C_{10}$ mononuclear aromatics | .23 | 1.94 |
| $C_{11}$–$C_{12}$ mononuclear aromatics | .2 | .23 |
| Naphthalene | 0 | 1.23 |
| *M-Naphthalenes | 0 | 3 |
| Total Wt. % Conversion | 8.56 | 55.69 |
| Wt. % $C_3H_8$ Conversion | 14.01 | 58.92 |
| Wt. % $C_6H_6$ Conversion | 14.01 | 53.73 |
| Wt. % Selectivity | | |
| $C_1$–$C_2$ | 5.96 | 13.68 |
| $C_4$ | 3.04 | 3.9 |
| $C_5$–$C_6$ | .35 | .43 |
| $C_7$+ aromatics | 90.54 | 81.99 |

EXAMPLE 14

A mixture of benzene and propane in a weight ratio of about 1:1 was fed continuously to a fixed bed isothermal tubular catalytic reactor. The bed is packed with a zinc-substituted ZSM-5 aluminosilicate catalyst of silica-to-alumina ratio equal to 70.

The reaction conditions are given in Table 14. The weight hourly space velocity (WHSV) of the feed is 1.3–2.9 and the continuous operation is conducted in the absence of hydrogen.

TABLE 14

| Charge (wt. %) | | |
|---|---|---|
| Propane | 47.7 | 50.9 |
| Benzene | 52.2 | 49 |
| Time on Stream (hrs.) | 4.9 | 25.2 |
| Temperature (°C.) | 468 | 468 |
| Pressure (kPa) | 137 | 137 |
| Catalyst Type .43% ZN - ZSM-5 ($SiO_2/Al_2O_3$ = 70) | | |

| Product formed | wt. % | wt. % |
|---|---|---|
| $C_1$ | 1.13 | 2.55 |
| $C_2$ | .78 | 1.91 |
| Iso-$C_4$ | .28 | .32 |
| N—$C_4$ | .65 | .76 |
| Iso-$C_5$ | .02 | .03 |
| N—$C_5$ | .03 | .04 |
| 2-M-$C_5$ | 0 | 0 |
| 3-M-$C_5$ | 0 | 0 |
| N—$C_6$ | 0 | 0 |
| *$C_{13+}$ | 0 | 0 |
| benzene (starting material) | 51.11 | 44.78 |
| propane (starting material) | 39.16 | 36.21 |
| toluene | 3 | 7.08 |
| $C_8$ aromatics | 2.23 | 3.47 |
| $C_9$ aromatics | .43 | .66 |
| $C_{10}$ mononuclear aromatics | .19 | .32 |
| $C_{11}$–$C_{12}$ mononuclear aromatics | .01 | .02 |
| Naphthalene | .29 | .7 |
| *M—Naphthalenes | .31 | .72 |
| Total Wt. % Conversion | 9.57 | 18.85 |
| Wt. % $C_3H_8$ Conversion | 17.87 | 28.85 |
| Wt. % $C_6H_6$ Conversion | 2.01 | 8.52 |
| Wt. % Selectivity | | |
| $C_1$–$C_2$ | 22.32 | 24.4 |
| $C_4$ | 9.82 | 5.99 |
| $C_5$–$C_6$ | .63 | .48 |
| $C_7$ + aromatics | 67.5 | 68.8 |

*Approximate Analysis

EXAMPLE 15

A mixture of benzene and propane in a weight ratio of about 1:1 was fed continuously to a fixed bed isothermal tubular catalytic reactor. The bed is packed with a zinc and rhenium exchanged H-ZSM-5 aluminosilicate catalyst of silica-to-alumina ratio equal to 35.

The reaction conditions are given in Table 15. The weight hourly space velocity (WHSV) of the feed is 3.3 and the continuous operation is conducted in the absence of hydrogen.

TABLE 15

| Charge (wt. %) | |
|---|---|
| Propane | 54.1 |
| Benzene | 45.8 |
| Time on Stream (hrs.) | 4.9 |
| Temperature (°C.) | 468 |
| Pressure (kPa) | 137 |
| Catalyst Type- Zn and Re exchanged ZSM-5 ($SiO_2/Al_2O_3$ = 35) | |

TABLE 15-continued

| Product formed | wt. % |
|---|---|
| $C_1$ | .42 |
| $C_2$ | 1.91 |
| Iso-$C_4$ | .42 |
| N—$C_4$ | .24 |
| Iso-$C_5$ | .02 |
| N—$C_5$ | .01 |
| 2-M-$C_5$ | 0 |
| 3-M-$C_5$ | 0 |
| N—$C_6$ | 0 |
| *$C_{13+}$ | 0 |
| benzene (starting material) | 47.28 |
| propane (starting material) | 44.83 |
| toluene | 1.17 |
| $C_8$ aromatics | 1.27 |
| $C_9$ aromatics | 1 |
| $C_{10}$ mononuclear aromatics | .26 |
| $C_{11}$-$C_{12}$ mononuclear aromatics | .02 |
| Naphthalene | .18 |
| *M—Naphthalenes | .2 |
| Total Wt. % Conversion | 9.22 |
| Wt. % $C_3H_8$ Conversion | 9.22 |
| Wt. % $C_6H_6$ Conversion | 0 |
| Wt. % Selectivity | |
| $C_1$-$C_2$ | 25.27 |
| $C_4$ | 7.16 |
| $C_5$-$C_6$ | .54 |
| $C_7$ + aromatics | 44.47 |

*Approximate Analysis

EXAMPLE 16

A mixture of benzene and propane in a weight ratio of about 1:1 was fed continuously to a fixed bed isothermal tubular catalytic reactor. The bed is packed with a platinum on H-ZSM-5 aluminosilicate catalyst of silica-to-alumina ratio equal to 70.

The reaction conditions are given in Table 16. The weight hourly space velocity (WHSV) of the feed is 1.3-1.5 and the continuous operation is conducted in the absence of hydrogen.

TABLE 16

| Charge (wt. %) | | |
|---|---|---|
| Propane | | |
| Benzene | | |
| Time on Stream (hrs.) | 4.8 | 24.8 |
| Temperature (°C.) | 426 | 440 |
| Pressure (kPa) | 5497 | 137 |
| Catalyst Type - .38% Pt - ZSM-5 ($SiO_2/Al_2O_3 = 70$) | | |

| Product formed | wt. % | wt. % |
|---|---|---|
| $C_1$ | 2.94 | .71 |
| $C_2$ | 16.32 | 2.47 |
| Iso-$C_4$ | 1.36 | 1.12 |
| N—$C_4$ | 1.58 | 1.66 |
| Iso-$C_5$ | .20 | .12 |
| N—$C_5$ | .13 | .12 |
| 2-M-$C_5$ | .02 | .01 |
| 3-M-$C_5$ | .01 | .01 |
| N—$C_6$ | .02 | .01 |
| *$C_{13+}$ | .21 | 0 |
| benzene (starting material) | 18.66 | 38.67 |
| propane (starting material) | 16.56 | 45.84 |
| toluene | 21.57 | 4.1 |
| $C_8$ aromatics | 10.87 | 2.73 |
| $C_9$ aromatics | 3.57 | .86 |
| $C_{10}$ mononuclear aromatics | 1.99 | .44 |
| $C_{11}$-$C_{12}$ mononuclear aromatics | .1 | .02 |
| Naphthalene | 1.07 | .19 |
| *M—Naphthalenes | 2.79 | .33 |
| Total Wt. % Conversion | 64.79 | 51.32 |
| Wt. % $C_3H_8$ Conversion | 64.47 | 15.19 |
| Wt. % $C_6H_6$ Conversion | 64.96 | 15.53 |
| Wt. % Selectivity | | |
| $C_1$-$C_2$ | 29.73 | 20.76 |
| $C_4$ | 4.54 | 18.15 |
| $C_5$-$C_6$ | .62 | 2.35 |
| $C_7$ + aromatics | 65.09 | 56.59 |

*Approximate Analysis

EXAMPLE 17

A mixture of benzene and propane in a weight ratio of about 1:1 was fed continuously to a fixed bed isothermal tubular catalytic reactor. The bed is packed with a nickel-exchanged (dried without washing off excess nickel) H-ZSM-5 aluminosilicate catalyst of silica-to-alumina ratio equal to 70.

The reaction conditions are given in Table 17. The weight hourly space velocity (WHSV) of the feed is 1.2-1.3 and the continuous operation is conducted in the absence of hydrogen.

TABLE 17

| Charge (wt. %) | | |
|---|---|---|
| Propane | 54.4 | 49.3 |
| Benzene | 45.5 | 50.5 |
| Time on Stream (hrs.) | 5.3 | 28.8 |
| Temperature (°C.) | 426 | 440 |
| Pressure (kPa) | 5497 | 137 |
| Catalyst Type - 4% Ni - H-ZSM-5 ($SiO_2/Al_2O_3 = 70$) | | |

| Product formed | wt. % | wt. % |
|---|---|---|
| $C_1$ | 4.58 | 1.06 |
| $C_2$ | 4.98 | 1.06 |
| Iso-$C_4$ | 1.86 | .28 |
| N—$C_4$ | 2.57 | .52 |
| Iso-$C_5$ | .26 | .02 |
| N—$C_5$ | .2 | .03 |
| 2-M-$C_5$ | .03 | 0 |
| 3-M-$C_5$ | .02 | 0 |
| N—$C_6$ | .03 | 0 |
| *$C_{13+}$ | .08 | 0 |
| benzene (starting material) | 19.32 | 48.48 |
| propane (starting material) | 27.97 | 41.4 |
| toluene | 17.36 | 3.61 |
| $C_8$ aromatics | 11.18 | 1.9 |
| $C_9$ aromatics | 4.37 | .42 |
| $C_{10}$ mononuclear aromatics | 2.21 | .22 |
| $C_{11}$-$C_{12}$ mononuclear aromatics | .2 | .02 |
| Naphthalene | .7 | .35 |
| M-Naphthalenes | 2.04 | .46 |
| Total Wt. % Conversion | 52.71 | 9.97 |
| Wt. % $C_3H_8$ Conversion | 48.55 | 16.09 |
| Wt. % $C_6H_6$ Conversion | 57.51 | 4.02 |
| Wt. % Selectivity | | |
| $C_1$-$C_2$ | 18.14 | 21.26 |
| $C_4$ | 8.4 | 8.12 |
| $C_5$-$C_6$ | 1.06 | .8 |
| $C_7$ + aromatics | 72.36 | 70.01 |

*Approximate Analysis

EXAMPLE 18

A mixture of benzene and propane in a weight ratio of about 1:1 was fed continuously to a fixed bed isothermal tubular catalytic reactor. The bed is packed with a chromium-exchanged H-ZSM-5 aluminosilicate catalyst of silica-to-alumina ratio equal to 70.

The reaction conditions are given in Table 18. The weight hourly space velocity (WHSV) of the feed is 1.3-1.4 and the continuous operation is conducted in the absence of hydrogen.

TABLE 18

| Charge (wt. %) | | |
|---|---|---|
| Propane | 50.2 | 51 |
| Benzene | 49.6 | 49 |
| Time on Stream (hrs.) | 5 | 25 |
| Temperature (°C.) | 426 | 440 |

TABLE 18-continued

| Pressure (kPa) | 5497 | 137 |
|---|---|---|
| Catalyst Type - 0.2% Cr (exchanged) H-ZSM-5 (SiO$_2$/Al$_2$O$_3$ = 70) | | |
| Product formed | wt. % | wt. % |
| C$_1$ | 5.48 | 1.16 |
| C$_2$ | 7.41 | 1.38 |
| Iso-C$_4$ | 1.43 | .97 |
| N—C$_4$ | 1.81 | 1.51 |
| Iso-C$_5$ | .19 | .08 |
| N—C$_5$ | .13 | .09 |
| 2-M-C$_5$ | .02 | .01 |
| 3-M-C$_5$ | .01 | 0 |
| N—C$_6$ | .02 | .01 |
| *C$_{13+}$ | .19 | 0 |
| benzene (starting material) | 14.86 | 44.33 |
| propane (starting material) | 18.74 | 41.77 |
| toluene | 22.7 | 4.21 |
| C$_8$ aromatics | 14.95 | 2.64 |
| C$_9$ aromatics | 5.85 | .64 |
| C$_{10}$ mononuclear aromatics | 2.34 | .35 |
| C$_{11}$-C$_{12}$ mononuclear aromatics | .3 | .03 |
| Naphthalene | .61 | .14 |
| *M—Naphthalenes | 2.92 | .25 |
| Total Wt. % Conversion | 66.39 | 13.74 |
| Wt. % C$_3$H$_8$ Conversion | 62.68 | 18.06 |
| Wt. % C$_6$H$_6$ Conversion | 70.05 | 9.16 |
| Wt. % Selectivity | | |
| C$_1$-C$_2$ | 19.42 | 19.07 |
| C$_4$ | 4.88 | 18.41 |
| C$_5$-C$_6$ | .57 | 1.67 |
| C$_7$+ aromatics | 75.1 | 60.12 |

*Approximate Analysis

EXAMPLES 19-20

Examples 1-18 above illustrate the effectiveness of converting benzene or toluene to alkylated aromatic materials in the presence of light alkanes such as ethane, propane or n-butane. The aromatics formed are predominantly C$_7$-C$_9$ materials and are obtained with relatively high selectivity.

The longer chain paraffins, by contrast, exhibit significantly lower selectivity to aromatics as a result of the cracking reactions which take place, as shown below.

A 50-50 wt. percent blend of benzene and n-heptane was used as the charge stock which was pumped into a downflow reactor through a Grove loader set at the specified pressure. Products were collected in a liquid nitrogen trap and analyzed by gas chromatography.

The catalysts and conditions employed are set out in Table 19 below.

TABLE 19

| | Benzene/Heptane Reaction | |
|---|---|---|
| Example | 19 | 20 |
| Catalyst Type | ZSM-5 | 750 |
| Temp., °F. | 600 | 750 |
| Pressure, psig | 400 | 400 |
| WHSV | 15 | 62 |
| H$_2$/HC | 3/1 | 7/1 |
| Products wt % | | |
| C$_1$ | 0 | .02 |
| C$_2$ | .1 | .5 |
| O$_2$ | 0 | .1 |
| C$_3$ | 4.5 | 8.2 |
| O$_3$ | .1 | .8 |
| iso-C$_4$ | 4.3 | 3.5 |
| n-C$_4$ | 3.4 | 5.6 |
| 1-O$_4$ | 0 | .05 |
| iso-O$_4$ | .04 | .2 |
| T—O$_4$ | 0 | .1 |
| C—O$_4$ | 0 | .04 |
| C$_5$'s | 2.8 | 3.7 |
| C$_6$'s | 1.1 | 1.4 |
| C$_6$H$_6$ | 39.7 | 38.4 |
| C$_7$'s | .9 | 1.8 |
| C$_7$H$_{16}$ | 24.8 | 18.6 |
| C$_8$'s | .3 | 2.3 |
| C$_9$'s | 13.6 | 9.3 |
| C$_{10}$'s | 2.3 | 2.4 |
| C$_{11}$'s | 1.3 | 1.5 |
| C$_{12}$'s | .6 | .7 |
| C$_{13}$'s | .2 | .5 |
| C$_{13+}$'s | .2 | .4 |
| Wt % C$_7$H$_{16}$ Reacted | 50.4 | 62.7 |
| Wt % C$_6$H$_6$ Reacted | 20.6 | 44 |
| Total Wt % Conv. | 35.5 | 42.9 |
| Material Balance | 101.1 | 100.7 |
| Product Selectivities | | |
| C$_1$-C$_6$ | 45.8 | 56 |
| C$_7$-C$_{13+}$ | 54.2 | 44 |
| C$_7$H$_{16}$/C$_6$H$_6$ | 2.44 | 2.71 |
| Wt % C$_7$-C$_{13+}$ | 19.2 | 18.9 |

EXAMPLES 21-28

The procedure of Examples 19 and 20 was repeated at atmospheric pressure using the same benzene:heptane feed at various conditions as set out in Table 20 below.

TABLE 20

| | Benzene/Heptane Reaction | | | | | | | |
|---|---|---|---|---|---|---|---|---|
| Example | 21 | 22 | 23 | 24 | 25 | 26 | 27 | 28 |
| Catalyst Type | Ni—H-ZSM-5 | HZSM-5 | H-ZSM-5 | H-ZSM-5 | H-ZSM-5 | H-ZSM-5 | H-ZSM-5 | H-ZSM-5 |
| WHSV | 1 | 1 | 1 | | | | | |
| Temp., °F. | 760 | 660 | 400 | 500 | 600 | 700 | 800 | 900 |
| H$_2$/HC | 5/1 | 3/1 | 3/1 | 3/1 | 3/1 | 3/1 | 3/1 | 3/1 |
| Wt % Products | | | | | | | | |
| C$_1$-C$_2$—O$_2$ | 1.0 | 1.5 | .7 | .6 | .8 | .8 | 1.8 | 4.8 * |
| C$_3$—O$_3$ | 20 | 16.6 | .6 | 5.6 | 12.9 | 17.2 | 24.1 | 28.5 |
| isdo-C$_4$ | 5 | 9.8 | 2.6 | 6.1 | 7.4 | 8.5 | 6.9 | 5.6 |
| n-C$_4$ | 9 | 9.6 | .3 | 6.1 | 11.2 | 11.6 | 9.1 | 1.9 |
| C$_5$'s | 2 | 4.3 | .4 | 4.7 | 5.2 | 3.6 | 1.6 | .8 |
| C$_6$'s | .2 | .9 | .2 | 1.5 | 1.0 | .5 | .4 | .1 |
| C$_6$H$_6$ | 40 | 38.5 | 49.5 | 43.6 | 42.7 | 37.6 | 36.1 | 38.6 |
| C$_7$H$_{16}$ | 5 | 2.3 | 43.9 | 20.6 | 6.5 | 2.2 | .4 | 0 |
| C$_7$'s (aromatics) | 2 | 2.5 | 0 | .2 | 1.1 | 2.8 | 4.9 | 7.4 |
| C$_8$'s | 9 | 7.4 | 0 | .3 | 3.6 | 9.3 | 9.2 | 7.7 |
| C$_9$'s | 2 | 1.9 | 1.9 | 8.5 | 5.1 | 1.7 | 1.5 | 1.2 |
| C$_{10}$'s | 2 | 1.9 | 0 | 1.3 | .4 | 1.7 | 1.4 | .9 |
| C$_{11}$'s | 1 | 1.1 | .0 | .5 | .8 | 1.1 | 1.4 | 1.7 |
| C$_{12}$'s | .6 | 1.2 | 0 | .3 | 1.1 | 1.1 | 1.0 | .8 |
| C$_{13}$'s | .1 | .4 | 0 | 0 | .3 | .4 | .4 | .4 |
| Total Wt % Conv. | 55 | 59.2 | 6.6 | 35.8 | 50.8 | 60.2 | 63.5 | 61.4 |
| Wt % C$_7$H$_{16}$ Reacted | 90 | 95.4 | 12.2 | 58.5 | 87.0 | 95.6 | 99.2 | 100 |

TABLE 20-continued

| Example | Benzene/Heptane Reaction | | | | | | | |
|---|---|---|---|---|---|---|---|---|
| | 21 | 22 | 23 | 24 | 25 | 26 | 27 | 28 |
| Wt % $C_6H_6$ Reacted | 20 | 23.0 | 1.0 | 12.8 | 14.6 | 24.8 | 27.8 | 22.8 |
| Selectivities | | | | | | | | |
| $C_1$–$C_6$ | 67.4 | 72.1 | 69.7 | 68.7 | 75.8 | 71.1 | 69.1 | 67.3 |
| $C_7$–$C_{13}+$ | 31.4 | 27.8 | 28.8 | 31.0 | 24.4 | 30.1 | 31.2 | 32.7 |
| $C_7H_{16}/C_6H_6$ | 4.5 | 4.15 | 12.2 | 2.21 | 3.11 | 3.86 | 2.57 | 4.39 |

In all cases above, the aromatic product selectivity ($C_7$–$C_{13}+$) is below 50 percent consistent with a mechanism involving cracking of the heptane feed.

We claim:

1. A process for producing alkylaromatics which comprises reacting a mononuclear aromatic compound and a $C_2$–$C_4$ paraffin in the presence of an acidic, intermediate pore size zeolite catalyst under substantially non-cracking conditions for the paraffin to produce $C_{7+}$ alkylaromatic products with a selectivity of at least 60 weight percent.

2. A process according to claim 1 in which the paraffin comprises propane.

3. A process according to claim 1 in which the aromatic compound comprises benzene.

4. A process according to claim 1 in which the non-cracking conditions include a temperature of about 325° C. to 480° C., pressure of about 2850 to 6875 kPa and weight hourly space velocity, based on active catalyst, of about 0.1 to 5.

5. A process according to claim 1 in which the paraffins comprise $C_2$–$C_4$ alkanes and the aromatics comprise benzene in a weight ratio of 10:1 to 1:10.

6. A process according to claim 1 in which the zeolite has a Constraint Index of 1 to 12.

7. A process according to claim 1 in which the zeolite has an acid cracking value of at least 50.

8. A process according to claim 1 in which the zeolite has a crystal size of about 0.02 to 1.0 microns.

9. A process according to claim 1 in which the zeolite comprises ZSM-5.

10. A process according to claim 1 which is carried out in the absence of added hydrogen.

11. A process for making alkyl aromatic hydrocarbons which comprise contacting a reaction mixture comprising benzene and propane in a weight ratio of 10:1 to 1:10 in the absence of added hydrogen at a temperature of about 315° C. to 480° C., a pressure of about 2850 to 6875 kPa and a weight hourly space velocity of about 0.1 to 5 WHSV, based on active catalyst, with a catalyst consisting essentially of at least one acidic metallosilicate zeolite having an acid cracking value of at least 50, a pore size of about 5 to 7 Angstroms, and a crystal size of about 0.02 to 1.0 microns and a Constraint Index of 1 to 12, thereby producing hydrocarbon product with at least 60 weight percent selectivity to $C_{7+}$ aromatics.

12. A process according to claim 11 in which the reaction mixture is contacted with the catalyst in the absence of added hydrogen.

13. A process according to claim 3 wherein the catalyst contains Bronsted acid sites which have been partially ion-exchanged with one or more metals from Groups I through VIII of the Periodic Table.

14. A process according to claim 3 wherein the catalyst comprises a zeolite having a ZSM-5 structure.

15. A process for preparing an alkyl aromatic hydrocarbon product comprising:
    maintaining a reaction zone containing an acidic metallosilicate zeolite catalyst having a crystal size of about 0.02 to 1.0 microns, a Constraint Index of 1 to 12 and an alpha value of at least about 50;
    contacting at reaction temperatures and a pressure of about 2750 to 13750 kPa and a WHSV of about 0.1 to 5 a feedstock comprising a mononuclear aromatic compound and a $C_2$–$C_4$ alkane with the catalyst in the reaction zone in the absence of added hydrogen to effectively convert about 20 wt. percent to 80 wt. percent of feedstock; and
    withdrawing a hydrocarbon product comprising at least 50 wt. percent alkylated aromatic compounds.

16. A process according to claim 15 in which the products are predominantly $C_7$ to $C_9$ alkylaromatic hydrocarbons.

17. A process according to claim 15 in which the zeolite comprises ZSM-5.

18. A process according to claim 15 in which the mononuclear aromatic compound comprises benzene.

19. A process according to claim 18 in which the alkane comprises propane.

20. A process according to claim 17 in which the alkylaromatic products are obtained in a selectivity of at least 50 weight percent.

* * * * *